United States Patent [19]

Clack et al.

[11] 3,972,681

[45] Aug. 3, 1976

[54] FLOW-THROUGH THERMAL DETECTOR

[75] Inventors: Peter Joseph Clack, Doylestown; Herman Wesley Levin, Philadelphia; George Clarence Mergner, Glenside, all of Pa.

[73] Assignee: Leeds & Northrup Company, North Wales, Pa.

[22] Filed: July 14, 1975

[21] Appl. No.: 595,949

[52] U.S. Cl. .............................. 23/253 R; 73/190 R; 195/103.5 C; 195/127
[51] Int. Cl.² ................. G01N 25/22; G01N 25/48; G01N 31/14
[58] Field of Search .......... 23/253 R, 254 R, 254 E, 23/255 E, 232 E; 338/34; 340/236; 195/103.5 C, 127; 73/190 R, 23, 116

[56] References Cited
UNITED STATES PATENTS

| 2,743,107 | 4/1956 | Cherry | 23/255 E |
|---|---|---|---|
| 2,821,462 | 1/1958 | McEvoy | 23/255 E |
| 3,076,697 | 2/1963 | Miller et al. | 23/254 E |
| 3,084,999 | 4/1963 | Davis | 23/255 E |
| 3,224,838 | 12/1965 | Evans et al. | 23/254 E |
| 3,436,190 | 4/1969 | Priestley et al. | 23/253 R |
| 3,460,909 | 8/1969 | Gayle | 23/254 E |
| 3,567,394 | 3/1971 | Betz | 23/232 E |
| 3,698,384 | 10/1972 | Jones | 23/255 E |
| 3,718,437 | 2/1973 | Paloniemi | 23/253 R |
| 3,801,973 | 4/1974 | Grabiel et al. | 23/254 E |

FOREIGN PATENTS OR APPLICATIONS

| 1,061,098 | 7/1959 | Germany | 23/254 E |

*Primary Examiner*—Morris O. Wolk
*Assistant Examiner*—Bradley R. Garris
*Attorney, Agent, or Firm*—William G. Miller, Jr.; Raymond F. MacKay

[57] ABSTRACT

A flow-through thermal detector for determining the temperature change resulting from a reaction in a fluid stream includes a pair of parallel fluid paths one of which carries the fluid stream in which the reaction occurs while the other carries a similar fluid without the occurrence of a reaction. The detector includes a temperature sensor for each path. The first of the sensors is mounted to sense the temperature of the reacting stream after said reaction has occurred while the second of the sensors is mounted to sense the temperature of the non-reacting stream at a point in its flow path comparable to that at which the first sensor is mounted. A heat shield is provided surrounding the parallel paths and the heat shield is controllable to a predetermined temperature. Preheating of the streams is carried out by a preheating means positioned within the heat shield to receive the fluid stream entering the shield. The preheating means is controlled to bring the fluid streams of the parallel paths to the same predetermined temperature to which the heat shield is controlled. The streams then enter an equalizing means surrounding that part of the paths between the preheating means and the region in which the reaction occurs for equalizing the temperatures of the streams in the parallel paths prior to the streams reaching the reaction region.

2 Claims, 2 Drawing Figures

FLOW-THROUGH THERMAL DETECTOR

BACKGROUND OF THE INVENTION

This invention relates to apparatus and methods for the determination of the heat of reaction between two reactants and more particularly it relates to the determination of the heat of reaction due to the reaction of a flowing solution of a particular constituent through an enzyme column wherein the purpose is to determine the concentration of the constituent in the solution.

For the purposes of this description the word "reaction" includes changes which result from both chemical and physical processes and, therefore, the word "reactant" is used to refer to an agent which takes part in such a process.

There are many approaches to measuring the heat of reaction. These approaches include the classical calorimetric methods and various types of flow-through calorimeters. The prior art approaches to flow-through measurement of heat of reaction have, however, not been sufficiently stable or sensitive to small changes in heat of reaction, particularly with regard to measurements involving small concentrations. Likewise, the prior art approaches have been too sensitive to flow changes for precise measurement.

It is therefore an object of this invention to provide a construction for a flow-through thermal detector which provides increased sensitivity, accuracy, and flow independence for the determination of the heat of reaction as, for example, in measuring the concentration of a reactant in a flowing liquid by measuring the heat of reaction caused by the exposure of that reactant to an enzyme, particularly where the enzyme is coupled to an inert carrier such as fine glass beads maintained in a reactor column.

SUMMARY OF THE INVENTION

The present invention contemplates a flow-through thermal detector for determining the temperature change resulting from a reaction in a fluid stream. The detector includes a pair of parallel fluid flow paths one of which carries the fluid stream in which the reaction occurs while the other path carries a similar fluid without the occurrence of a reaction. The detector includes a temperature sensor for each path. The first of the sensors is mounted to sense the temperature of the reacting stream after said reaction has occurred while the second of the sensors is mounted to sense the temperature of the non-reacting stream at a point in its flow path comparable to that at which the first sensor is mounted. The heat shield is provided surrounding the parallel paths and the heat shield is controllable to a predetermined temperature. Preheating means is provided surrounding a part of the paths up-stream from the reaction region. The preheating means is positioned within the heat shield to receive the fluid stream entering the shield and is controlled to bring the fluid streams of the parallel paths to the same predetermined temperature to which the heat shield is controlled. The streams then enter an equalizing means surrounding the part of the paths between the preheating means and the region in which the reaction occurs to bring the temperature of the streams to the same temperature prior to the streams reaching the reaction region.

DESCRIPTION OF THE PREFERRED EMBODIMENT

Figure 1:
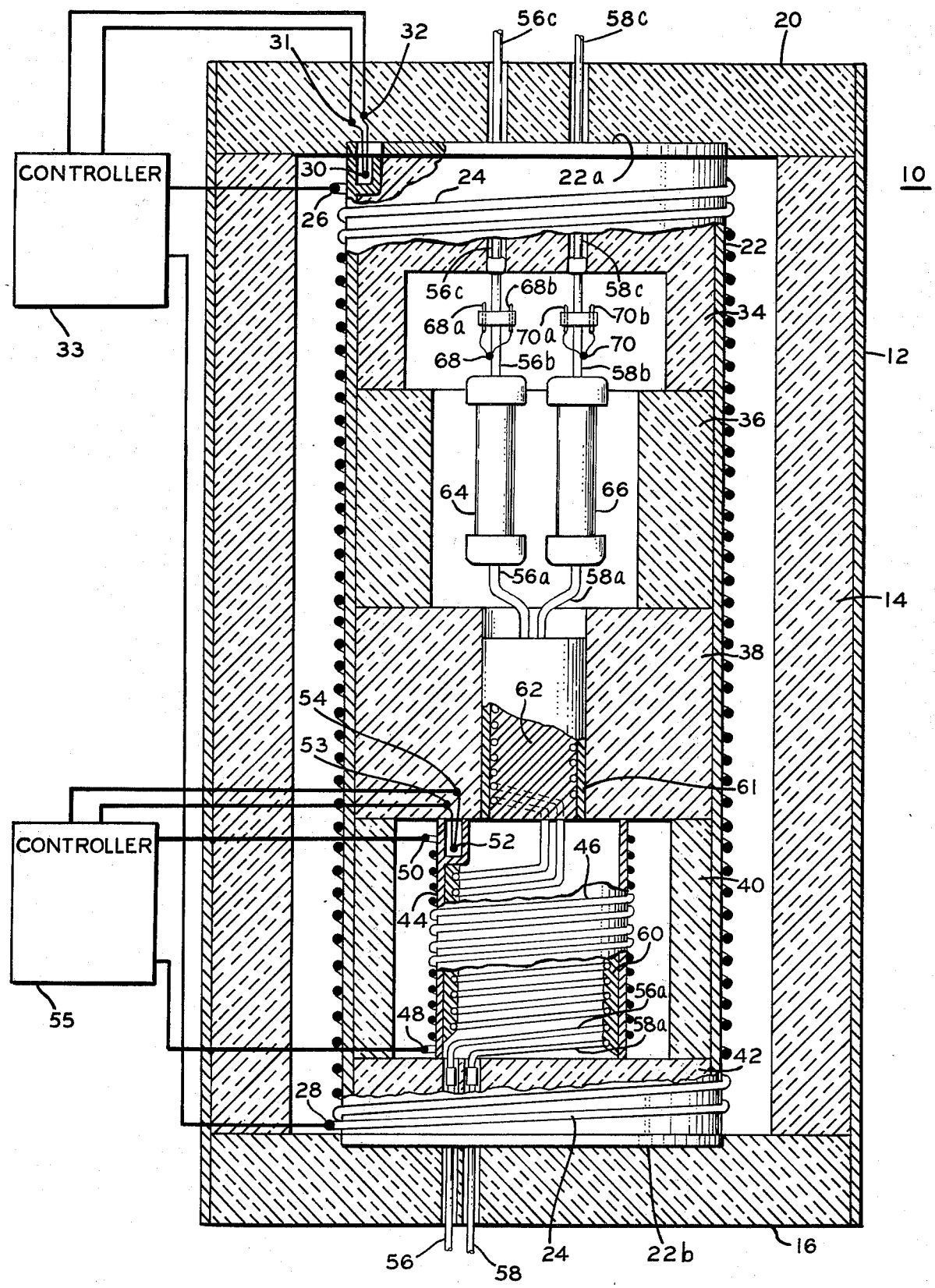
FIG. 1 is a cross-section of the flow-through thermal detector of this invention.

In FIG. 1 the flow-through thermal detector 10 is shown with an external cylindrical thermal equalizer 12 which may, for example, be a section of copper tubing. That equalizer contains blocks of insulating material such as the cylindrical block 14 and circular blocks 16 and 20 which may, for example, be an insulating material such as Ethafoam or any other suitable material with good insulating qualities. Those blocks of insulation form an insulating cover for the heat shield of the flow-through detector, namely, the cylindrical case 22 which may, for example, also be of copper. The case 22 and its associated end plates 22a and 22b are shown with a heater coil 24 wrapped around the periphery of the case 22 and extending between the terminals 26 and 28.

The temperature of the shield is detected by a temperature sensor such as a thermistor 30 located in contact with the inside of the case 22 at the upper end. The thermistor 30 is shown as being connected electrically to the two contacts 31 and 32.

Within the heat shield 22 there are provided a number of blocks of insulating material 34, 36, 38, 40, and 42 which serve to insulate from the shield the elements in the flow paths carrying two parallel streams through the detector which elements will now be described.

A pair of plastic tubes 56 and 58 are provided for the purpose of introducing into the detector the two parallel flowing streams which are of the same fluid, a constituent of which is to be analyzed for the purpose of determining the concentration of that constituent or reactant. The tubes 56 and 58 enter the thermal equalizer 12 through the circular insulating block 16 and then go directly through the circular insulating block 42. As the tubes pass through insulating block 42 they are connected to stainless steel tubes 56a and 58a, respectively. Tubes 56a and 58a then provide the continuing passages into the first chamber 44, which is for preheating the streams. In the chamber 44 the tubes 56a and 58a are coiled in the form of a spiral in intimate thermal contact with the inner wall of the chamber 44. The intimate thermal contact between the body of the chamber 44 and the tubes is increased by covering the tubes with tin as indicated by the reference character 60. The tin may, for example, be flowed over the tube spirals so as to completely cover them and maintain them in good thermal contact with the inner wall of the chamber 44.

By controlling the current through the heater coil 46 which is wrapped around cylinder 44 it is possible to maintain a very close control of the temperature within the chamber 44. That temperature is sensed in the exit area of the chamber 44 by the thermistor 52 which has its terminals 53 and 54 connected to a control instrument 55 so that that control instrument can effect a control of the current flowing through the coil 46 by virtue of its connection to the terminals 48 and 50. The control of the heater current in response to the temperature measured by means of the thermistor may be by a simple proportional control response.

The coils 56a and 58a may, for example, be assumed to be carrying a sucrose solution from a single source which has been previously divided so that the solution is provided to the tubes 56 and 58 at equal and substantially constant flow rates as, for example, by means of a dual peristaltic pump.

The size of chamber 44 and the length of the coils 56a and 58a within the chamber combine with the heating capacity of heater 46 to determine the range over which the flow of the fluid streams in tubes 56a and 58a can vary and still reach the set point temperature for controller 55 as is necessary to maintain the overall flow independence of the detector.

The tubes 56a and 58a exit from the first chamber 44 at its upper end with their fluid streams at a predetermined temperature slightly higher than the temperature at which the fluid entered 56 and 58. That predetermined temperature is determined by the set point established for controller 55 which should preferably be set at the same value as the set point for controller 33 controlling the temperature of the heat shield.

The tubes 56a and 58a immediately enter the lower end of a second chamber 61 after exiting chamber 44. In chamber 61 the tubes are spiraled to form a coil along the inside wall of the chamber. The chamber 61 may have its outside walls consisting of copper. As shown in FIG. 1, the chamber 61 is filled with a good heat conductive substance indicated by the reference character 62. That substance may, for example, be zinc so that the second chamber then comprises an outer shell 61 which may be copper which contains the coiled tubes 56 and 58 in a spiral along the inner surface of the shell with the entire cavity of the shell being filled with zinc so that as the tubes 56 and 58 exit from the chamber 61 any slight differences in temperature between the flowing streams which may have existed as they exited from the first chamber has been essentially eliminated. Chamber 61 is thus a temperature equalizing chamber which is effective to bring the flowing streams in tubes 56a and 58a to essentially the same temperature as they enter the reaction region of the flow path through the detector 10. That region includes the columns 64 and 66, which are connected to tubes 56a and 58a, respectively.

One of the columns, column 66, is the reactor column. That is the column in which the reaction occurs. It contains a reactant, which in this case may be the enzyme invertase, which is maintained in the column by being immobilized on the surface of small glass beads packed in the column. As the stream of sucrose solution flows through column 66 the enzyme catalyzes the hydrolysis of the sucrose and produces the normal heat of reaction which accompanies such a chemical change. The quantity of enzyme should be such that the reaction goes to completion when the fluid flow rate of the stream in tube 58a is within the expected flow range to prevent any flow dependence due to the reaction itself.

The column 64, on the other hand, is the dummy column and for purposes of similarity with the column 66 it would, in the specific application being described, be packed with glass beads of the type utilized in column 66 with the exception that the glass beads in the column 64 would not contain, immobilized on their surfaces, any enzyme so that the column 64 would not contain any material causing a chemical change in the flowing stream entering it through the tube 56a. However, any frictional heat developed by flowing the stream from tube 58a over the beads in column 66 would be matched by a similar frictional heat being produced in column 64 so that there would be no flow dependence introduced by column 64.

In addition the use of column 64 tends to eliminate effects resulting from changes in the temperature of the fluid stream which may be beyond the range normally eliminated after flow chambers 44 and 61. The columns 64 and 66 may be constructed of plastic material, for example, with the ends appropriately sealed to the tubes 56a and 58a at one end and to the exit tubes 56b and 58b at the other end. The tubes 56b and 58b are also preferably of a heat conducting material such as stainless steel, as are tubes 56a and 58a.

The tubes 56b and 58b are then used to measure the temperature of the material flowing through them. That is accomplished by the use of temperature sensors such as thermistors 68 and 70 shown as being mounted in intimate contact with the tubes 56b and 58b, respectively. The thermistors 68 and 70 are each connected by means of fine wire to terminals 68a and 68b in the one case and terminals 70a and 70b in the other case.

The tubes 56b and 58b are joined to the exit tubes 56c and 58c which may, for example, be of plastic. The tubes 56c and 58c then exit from the heat shield 22 and through the insulating block 20 from the thermal equalizer formed by the outside case 12.

It will be evident from consideration of the above description of the flow-through detector 10, that the separate flowing streams introduced through the tubes 56 and 58 are first subjected in the first chamber 44 to the application of heat as necessary to bring the temperatures of the two flowing streams as closely as possible to the same predetermined temperature which will normally be slightly elevated from the temperature of those streams prior to their introduction into the detector. The two streams are then introduced into the second chamber which is essentially for further equalizing the stream temperatures and provides a means for filtering out any differences which may occur in the temperature between the flowing streams so that the two streams arrive at the columns 64 and 66 at substantially the same temperature and at substantially the same flow rate.

One of the streams then flows through the reactor column while the other flows through a dummy column and the temperatures of the streams as they exit from the columns are compared, as will be explained, so as to determine the temperature difference therebetween as a measure of the concentration of the constituent in the streams. As shown in FIG. 1, the temperatures of the first and second chambers as well as the columns are maintained substantially constant at a predetermined elevated value by virtue of the temperature detector 30 which is connected to a controller 33 to control by proportional control action the current flow through the heater 24. By virtue of the connection of the controller 33 to terminals 26 and 28 the temperature within the heat shield 22 is maintained substantially constant at the same value as that maintained at the exit of chamber 44 and hence close to the temperature of the streams of fluid entering the columns. It is important that the temperature of the solutions entering the columns be the same as the temperature of the surrounding shield 22 so that there will be no net flow of heat to or from the columns except that due to heat generated in the columns.

Figure 2:
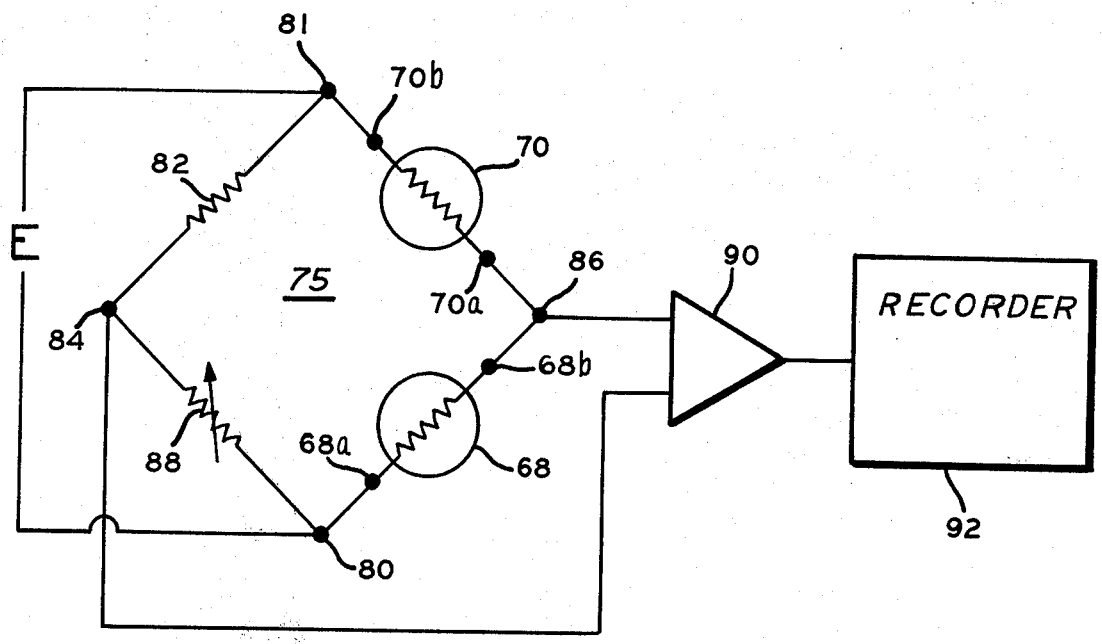
FIG. 2 is a circuit diagram showing the manner in which the temperature difference between the fluids exiting from the columns of the thermal detector is measured.

The temperatures detected by the thermistor 68 and the thermistor 70 are compared in a bridge circuit such as that shown in FIG. 2 wherein the thermistor 68 is shown in one arm of the bridge 75 with the thermistor 70 being in a comparable arm of the other side of the bridge. The bridge 75 is supplied from a potential source E, that is connected across terminals 80 and 81, with a fixed resistor 82 connected between terminal 81 and one of the output terminals 84 with the thermistor 70 being between the terminal 81 and the other output terminal 86. As shown in FIG. 2, a variable resistor 88 is utilized in the branch of the bridge circuit between the terminals 80 and 84 as a means for standardizing the bridge when the thermistors 68 and 70 are at the same temperature.

The amplifier 90 is connected across the bridge output terminals 84 and 86 and in turn drives the recorder 92 to produce an indication and a record of the temperature difference detected by thermistors 68 and 70.

It may be desirable in the construction of the thermal detector of FIG. 1 to add a cylindrical thermal equalization member positioned between the cylinder 22 and the elements contained therein and insulated from both. That member could also be of copper and would serve to help equalize the temperature along the length of the detector. Other variations which might also be desirable include the returning of tubes 56c and 58c to the end of the detector at which 56 and 58 enter. Those tubes could, for example, be returned by passing them through insulating blocks 34, 36, 38, 40, 42, and 16. If the additional thermal equalizer mentioned above is used then the tubes 56c and 58c could be returned in a path between the added thermal equalizer and cylinder 22.

Thermal detectors using the novel structure of FIG. 1 but differing in certain respects may be constructed for using the novel structure for reactions other than those involving enzymes immobilized on glass beads and packed in a reactor column. Thus, for example, a reactant such as an enzyme, which reacts with the constituent of the flowing streams may be introduced into the reaction region of one of the flow paths by another separate flow path if the reactant is in liquid form, for example.

What is claimed is:

1. Apparatus for measuring the concentration of a constituent of a liquid stream by measuring the heat of chemical reaction between the constituent and a reactant comprising a heat shield having walls of thermally conductive material,
heat insulating material surrounding said walls,
means for heating the walls of said shield,
means for detecting the temperature of the walls of said shield,
means responsive to the temperature detected by said detecting means for controlling the heating of said shield to maintain its temperature at a predetermined value,
a first chamber adapted to receive two streams of said liquid upon entry of said streams into said shield, said chamber having thermally conductive walls spaced from said case and means defining a long path for said streams in said chamber,
means for heating the walls of said first chamber,
means for sensing the temperature of the walls of said first chamber,
means responsive to the sensed temperatures of said walls of said first chamber for controlling the heating of said first chamber to maintain its temperature at a desired value corresponding with said predetermined temperature of said shield,
a second chamber in said shield, said second chamber comprising thermally conductive material adapted to have passages for receiving the liquid flowing from said first chamber,
a reactor column for receiving one of said flowing liuid streams after it has passed through said second chamber and for putting that stream in contact with said reactant,
a dummy column for receiving the other of said flowing liquid streams after it has passed through said second chamber, said dummy column being of similar construction to said reactor column with the omission of said reactant,
means for heat insulating said first and second chambers and said columns from said shield,
temperature sensing means at the exit end of each of said columns for sensing the temperature of said liquid stream, and
means responsive to both of the sensed temperatures for measuring the difference between the temperature of the liquid streams at the exit end of each column as an indication of the concentration of said constituent.

2. A flow-through thermal detector for measuring the concentration of a constituent of a flowing stream by measuring the temperature change produced by a chemical reaction occurring when said stream contacts a reactant comprising, a heat shield of thermally conductive material covered by insulating material,
a heater coil wrapped around said shield,
a first temperature sensor for measuring the temperature of said shield,
a first controller responsive to the first temperature sensed by said sensor for varying the currents through said heater to maintain the temperature of said shield at a predetermined point,
a pair of tubes for carrying the fluid of said stream into the shield,
a first thermally conductive chamber for receiving said fluid when it enters said shield, said first chamber having said pair of tubes coiled along the inner wall and in intimate thermal contact therewith,
a heater element wound around the walls of said first chamber so as to be in good thermal contact therewith,
a second temperature sensor in thermal contact with the inner wall of said first chamber at its exit end,
a second controller connected with said second sensor and operable to modify the current flow through said heater around said chamber to bring the temperature of the fluid in the pair of tubes to a predetermined value corresponding with the temperature of said shield,
A second chamber in said shield for receiving said pair of tubes after they exit from said first chamber, said second chamber having said tubes coiled therein along the inside walls with the space not occupied by said tubes being filled with a good heat conductive substance so as to tend to even out the variations in temperature of the fluid in said tubes, a reactor column for receiving the fluid from one tube after it exits from said second chamber for reaction of the fluid upon contact with a reactant, a dummy column for receiving said fluid from the other of said tubes after it exits said second chamber for flow therethrough without chemical reaction, insulating means interposed to substantially fill the space in said shield between said chambers, columns, and tubes, a third temperature sensor at the exit area of each of said columns, temperature difference measuring means operable in response to the temperature detected by said third sensors at the exits of said columns for measuring said concentration.

* * * * *